United States Patent [19]

Baer et al.

[11] 4,426,715
[45] Jan. 17, 1984

[54] RADIATION DIAGNOSTIC APPARATUS

[75] Inventors: Ulrich Baer, Nuremberg; Walter Distler, Erlangen-Dechsendorf; Peter Grassmann, Erlangen, all of Fed. Rep. of Germany

[73] Assignee: Siemens Aktiengesellschaft, Berlin & Munich, Fed. Rep. of Germany

[21] Appl. No.: 394,137

[22] Filed: Jul. 1, 1982

[30] Foreign Application Priority Data

Jul. 6, 1981 [DE] Fed. Rep. of Germany ....... 3126643

[51] Int. Cl.³ .............................................. A61B 6/02
[52] U.S. Cl. ............................................ 378/4; 378/20
[58] Field of Search ...................... 378/14, 4, 20, 208, 378/209, 10, 17

[56] References Cited
U.S. PATENT DOCUMENTS

| | | | |
|---|---|---|---|
| 3,778,614 | 12/1973 | Hounsfield | 378/901 |
| 4,002,917 | 1/1977 | Mayo | |
| 4,112,303 | 9/1978 | Brandt | 378/17 |
| 4,316,091 | 2/1982 | Bernardi | 378/17 |
| 4,352,986 | 10/1982 | Pfeiler | 378/14 |

Primary Examiner—Alfred E. Smith
Assistant Examiner—T. N. Grigsby
Attorney, Agent, or Firm—Hill, Van Santen, Steadman & Simpson

[57] ABSTRACT

An exemplary embodiment comprises a patient support, a radiation source which generates a radiation beam penetrating the radiography subject, a radiation receiver which converts the radiation intensity behind the subject into electric signals, a measurand converter for the conversion of the electric signals delivered by the radiation receiver into an optically visible image, and a rotating frame assembly on which the radiation source and the radiation receiver are mounted and which, for the purpose of scanning the radiography subject from various directions, is rotatably mounted about an axis extending in the longitudinal direction of the patient support. The rotating radiation source is adjustable in the longitudinal direction of the patient support jointly with movement of the patient support so that several parallel transverse layers of the radiography subject can be very rapidly scanned.

1 Claim, 5 Drawing Figures

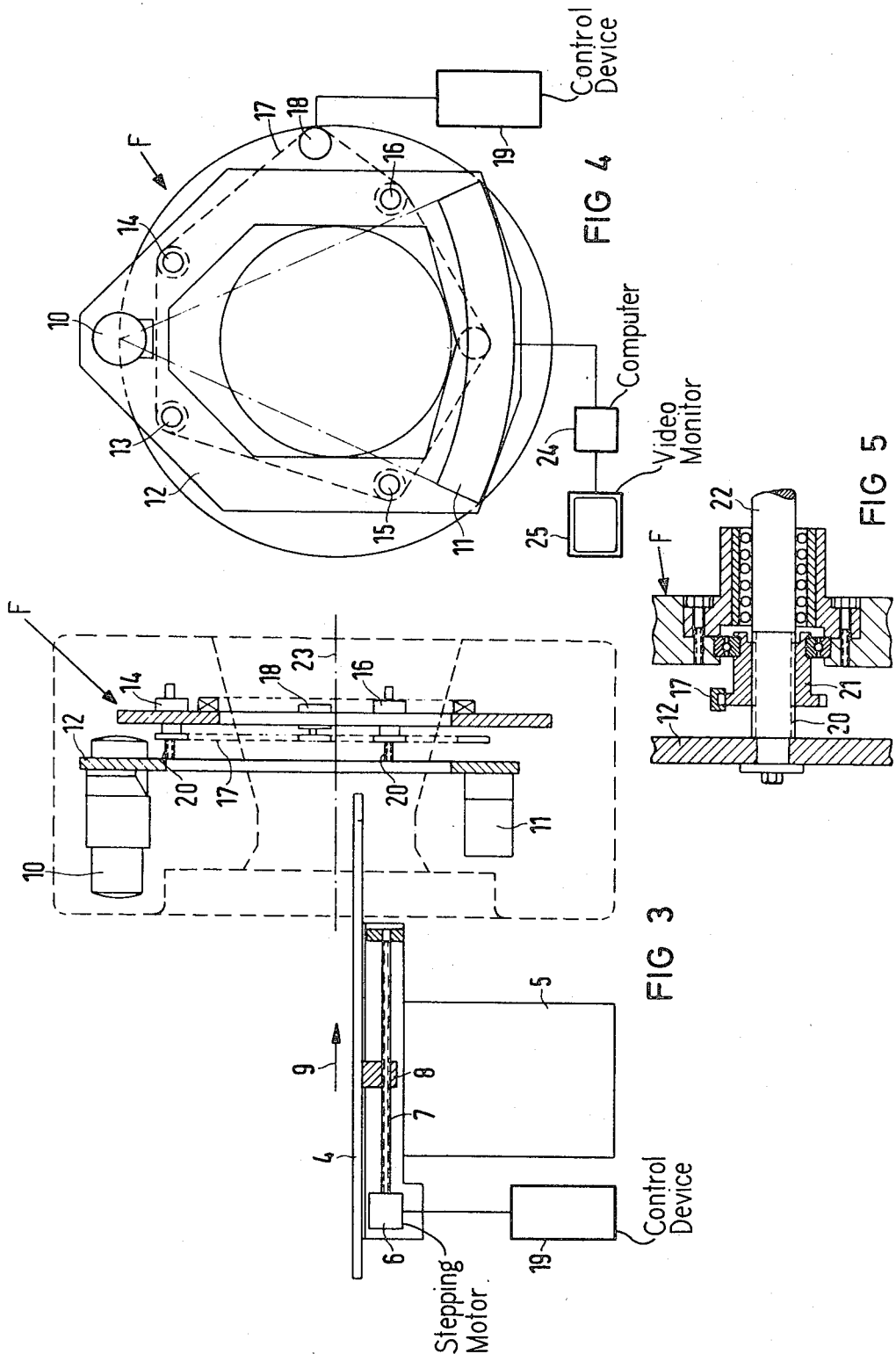

RADIATION DIAGNOSTIC APPARATUS

BACKGROUND OF THE INVENTION

The invention relates to a radiation diagnostic apparatus for producing transverse layer images of a radiography subject, comprising a patient support, a radiation source which generates a radiation beam penetrating the radiography subject, a radiation receiver which converts the transmitted radiation intensity behind the subject into electric signals, a measured value converter for the conversion of the electric signals supplied by the radiation receiver into an optically visible image, and a rotating frame on which the radiation source and the radiation receiver are mounted and which, for the purpose of scanning the radiography subject from different directions, is rotatably mounted about an axis extending generally parallel to the longitudinal direction of the patient support.

A radiation diagnostic apparatus of this type is described in the German OS No. 25 59 658 (U.S. Pat. No. 4,002,917). This radiation diagnostic apparatus, designated as a computer tomograph, permits the scanning of several parallel layers of the radiography subject. To this end, the elements of the radiation receiver extend in a direction generally parallel to the longitudinal direction of the patient support over the set of layers to be scanned. The X-ray tube exhibits an anode on which a deflectable electron beam activates focal spots at specified locations so that, given corresponding collimation, different layers are irradiated. A different part of the elements of the radiation receiver—viewed in the longitudinal direction of the patient support—is here irradiated with X-rays in each instance. The various focal spots are activated by means of deflection of the electron beam of the X-ray tube.

The known radiation diagnostic apparatus permits, in a very brief time, the scanning of several parallel layers of the radiography subject; however, it is constructed in a very complicated fashion because it requires, in particular, a special X-ray tube.

Also with a computer tomograph, in which a conventional X-ray tube is employed with a focal spot which is stationary relative to the tube, the scanning of several parallel layers of the radiography subject is possible if, subsequent to scanning of one layer, the patient support is displaced in the longitudinal direction and then the next layer is scanned. However, in order to scan several parallel layers, a relatively large amount of time is necessary for this purpose.

SUMMARY OF THE INVENTION

The object underlying the invention resides in producing a radiation diagnostic apparatus of the type initially cited in which, with a conventional X-ray tube, a very rapid scanning of several parallel layers of the radiography subject is possible.

In accordance with the invention, this object is achieved in that the rotating frame is constructed for moving the X-ray tube in the longitudinal direction of the patient support. In the inventive X-ray diagnostic apparatus, during scanning of a transverse layer of the radiography subject, the patient support can be moved and with the same speed, the radiation source can be adjusted in step with the movement of the patient support.

Following termination of a scanning operation, the X-ray source can then be shifted back into its initial position and the scanning of a parallel transverse layer of the radiography subject can proceed, whereby during the scanning again the rotating X-ray source together with the patient support is displaced. This operation can be repeated many times for the purpose of scanning several parallel layers. A continuous longitudinal displacement of the radiography subject can thus take place. Accordingly, the scanning is terminated in a relatively short time.

The invention shall be explained in greater detail in the following on the basis of the accompanying drawing sheets; and other objects, features and advantages will be apparent from this detailed disclosure and from the appended claims.

BRIEF DESCRIPTION OF THE DRAWING

FIGS. 3 and 4 show two views of a radiation diagnostic apparatus according to the invention; and FIG. 5 shows a detail of the radiation diagnostic apparatus according to the FIGS. 3 and 4.

DETAILED DESCRIPTION

Figure 1:
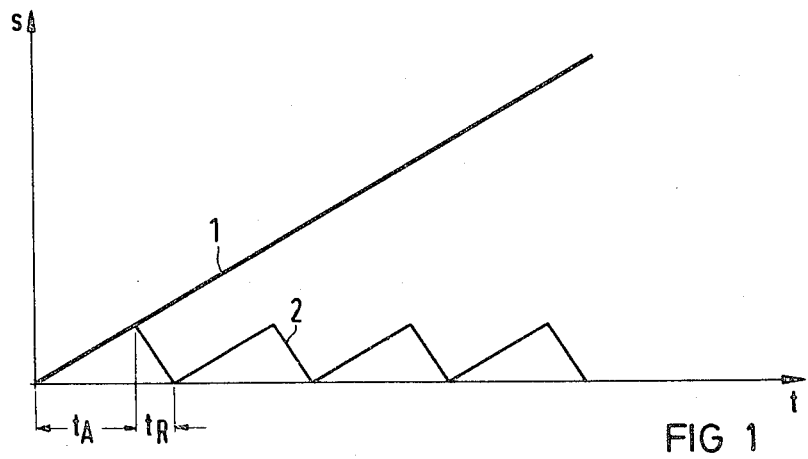
FIG. 1 illustrates a speed diagram for representing a first movement possibility of the rotating X-ray source in the case of a radiation diagnostic apparatus according to the invention.

In FIG. 1, line 1 represents the displacement as a function of time of the patient support of a radiation diagnostic apparatus according to the invention during the scanning of successive patient layers. Curve 2 shows the speed variation in the support-longitudinal direction of the rotating X-ray source. Within the times such as $t_4$ the rotating frame is adjusted with the same speed as the patient support in the support-longitudinal direction and a scanning of a transverse layer of the radiography subject takes place through rotation of the rotating frame through an angle of, for example, 360°. In the following times such as $t_R$ the rotating frame is set back to its initial position so that it is ready for the scanning of a layer parallel to the previously scanned layer.

Figure 2:
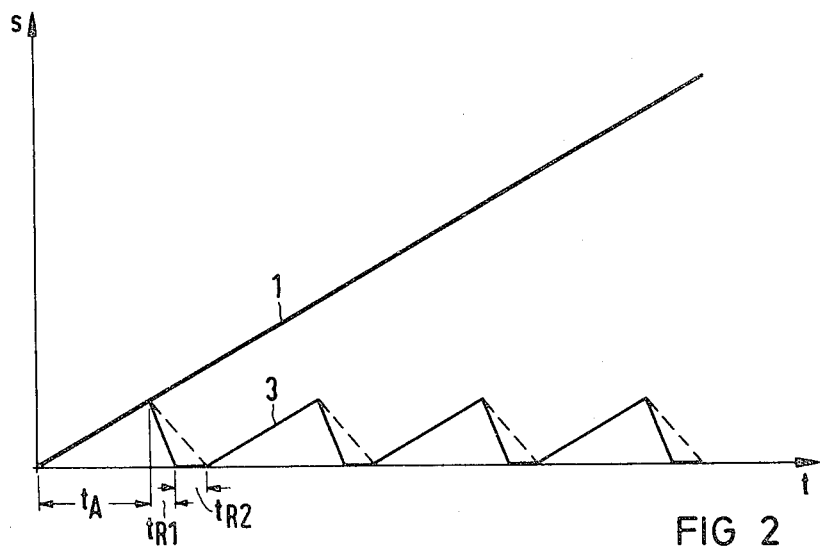
FIG. 2 shows a speed diagram representing a second movement possibility in the case of a radiation diagnostic apparatus according to the invention.

Underlying the curve progression of FIG. 2 is again the line 1. Curve 3 shows that the time between scans (corresponding to $t_R$ in FIG. 1) is subdivided into two time sections such as $t_{R1}$ and $t_{R2}$. The resetting of the rotating frame proceeds in the intervals such as $t_{R1}$, whereas no scanning takes place in the intervals such as $t_{R2}$. Accordingly, where the sum of time intervals $t_{R1}$ and $t_{R2}$ is greater than the time interval $t_R$ in FIG. 1, given the same slope of line 1, the distance between the parallel scanned layers is greater for the case of FIG. 2 than for the case with a speed progression according to FIG. 1.

In FIG. 3, a patient support 4 is illustrated which is displaceably mounted on a base 5 with the aid of a stepping motor 6, an externally threaded shaft 7, and an internally guide 8 which is movable in the longitudinal direction, i.e. in direction of the arrow 9. Serving the purpose of scanning a transverse layer of a patient lying on the support 4 are an X-ray tube 10 and a radiation receiver 11 which are mounted opposite one another on a carrier 12 of a rotating frame assembly F. The carrier 12 of the rotating frame assembly is adjustably mounted for displacement of the X-ray tube 10 and the radiation receiver 11 in the longitudinal direction of the support 4. To this end, the frame assembly is provided with, in the example, four, column guides 13 through 16 about which a chain 17, illustrated in FIG. 4, is guided which is driven by a motor 18. The motors 6 and 18 are controlled by a control device 19.

FIG. 5 illustrates the embodiment of one of the column guides 13 through 16. From FIG. 5 it is apparent that each column guide exhibits a threaded part 20 which is guided in a nut 21 which is rotated by the chain 17. During the rotation of the nut 21 the column 22 moves in its longitudinal direction in ball bearings and thus shifts the carrier 12 of the rotating frame assembly F in the support-longitudinal direction.

The scanning of several parallel layers of a patient on the support 4 proceeds in such a manner that first the support 4 and the carrier 12 of the rotating frame assembly F are moved with the same speed in the direction of the arrow 9 with the aid of the motors 6 and 18, whereby the carrier 12 together with the other parts of the frame assembly F is additionally rotated by means of a known rotary drive about the axis 23, so that the patient on the support 4 is irradiated from different directions. The radiation receiver 11, which is comprised of a series of detector elements, receives the radiation issuing from the patient and delivers electric signals which correspond to the respectively received radiation intensity. From these signals a computer 24 computes the attenuation coefficients of an image matrix which can then be displayed in the form of an image of the irradiated transverse layer of the patient on a monitor 25. After complete scanning of a transverse layer, the motor 18 is reversed in polarity, so that it moves the carrier 12 back into the original starting position (FIG. 3); namely, with a higher speed than the speed with which the scanning took place. Subsequently, the stepping motor 18 is again switched on in the counter direction so that the carrier 12 is shifted synchronously with the support 4 with the same speed for the scanning of the next parallel transverse layer.

It will be apparent that many modifications and variations may be made without departing from the scope of the teachings and concepts of the present invention.

We claim as our invention:

1. Radiation diagnostic apparatus for producing transverse layer images of a radiography subject, comprising a patient support, a radiation source which generates a radiation beam penetrating the radiography subject, a radiation receiver which converts the radiation intensity behind the subject into electric signals, a measurand converter for the conversion of the electric signals supplied by the radiation receiver into an optically visible image, and a rotating frame assembly on which the radiation source is mounted and which, for the purpose of scanning the radiography subject from various directions, is rotatably mounted about an axis extending in a longitudinal direction generally longitudinally of the patient support, characterized in that the rotating frame assembly comprises a carrier for the X-ray source which is adjustably mounted for movement in the longitudinal direction, characterized in that driving means for the movement of the patient support and the carrier of the rotating frame assembly in the longitudinal direction are so designed that the patient support and the X-ray source, during its rotation with the rotating frame assembly, are moved longitudinally with the same speed, and that, following termination of this rotation, the return of the carrier into an initial position proceeds with a higher speed.

* * * * *